US007772296B2

(12) United States Patent
Garey, Jr. et al.

(10) Patent No.: US 7,772,296 B2
(45) Date of Patent: Aug. 10, 2010

(54) ANTIMICROBIAL POLYURETHANE RESINS AND PRODUCTS MADE THEREFROM

(75) Inventors: Harold Elbridge Garey, Jr., Methuen, MA (US); Andrew Martin Reed, Arvada, CO (US)

(73) Assignee: Advansource Biomaterials Corporation, Wilmington, MA (US)

( * ) Notice: Subject to any disclaimer, the term of this patent is extended or adjusted under 35 U.S.C. 154(b) by 543 days.

(21) Appl. No.: 11/811,138

(22) Filed: Jun. 8, 2007

(65) Prior Publication Data

US 2008/0306181 A1    Dec. 11, 2008

(51) Int. Cl.
| | |
|---|---|
| C08K 3/10 | (2006.01) |
| C08K 3/32 | (2006.01) |
| C08K 3/36 | (2006.01) |
| C08K 3/40 | (2006.01) |
| C09D 5/18 | (2006.01) |
| A61F 2/02 | (2006.01) |
| A61K 8/87 | (2006.01) |

(52) U.S. Cl. .................. 523/105; 523/113; 523/122; 524/403; 524/413; 524/423; 524/492; 524/494; 524/779; 524/780

(58) Field of Classification Search .............. 524/403, 524/413, 423, 492, 494, 779, 780; 523/105, 523/113, 122
See application file for complete search history.

(56) References Cited

U.S. PATENT DOCUMENTS

| 5,254,662 | A  | 10/1993 | Szycher et al. ............. 528/673 |
| 5,863,627 | A  | 1/1999  | Szycher et al. ............. 428/36.8 |
| 6,305,423 | B1 | 10/2001 | De Meyer et al. ............. 138/33 |
| 6,342,212 | B1 | 1/2002  | Schuette et al. ............ 424/78.1 |
| 6,448,306 | B1 | 9/2002  | Lever et al. ................. 523/122 |
| 6,454,813 | B1 | 9/2002  | Chan ........................ 8/115.51 |
| 6,455,115 | B1 | 9/2002  | DeMeyer ................... 428/36.2 |
| 6,455,610 | B1 | 9/2002  | Lever et al. ................. 523/122 |
| 6,460,575 | B1 | 10/2002 | De Meyer et al. ........... 138/125 |
| 6,461,386 | B1 | 10/2002 | Chan et al. ................. 8/115.51 |
| 6,479,144 | B2 | 11/2002 | Petrea et al. ................. 428/379 |
| 6,544,621 | B1 | 4/2003  | Schuette et al. .............. 428/97 |
| 6,555,599 | B2 | 4/2003  | Lever et al. ................. 523/122 |
| 6,593,260 | B2 | 7/2003  | Nomura ...................... 501/48 |
| 6,624,277 | B2 | 9/2003  | Yahkind et al. ............. 528/45 |
| 6,627,281 | B2 | 9/2003  | DeMeyer .................. 428/36.1 |
| 6,638,993 | B2 | 10/2003 | Patel et al. .................. 523/122 |
| 6,663,808 | B2 | 12/2003 | DeMeyer .............. 264/171.26 |
| 6,769,146 | B2 | 8/2004  | Copeland et al. ............... 5/653 |
| 6,815,379 | B2 | 11/2004 | Nomura ...................... 442/123 |
| 6,833,335 | B2 | 12/2004 | DeMott et al. ................ 442/94 |
| 6,846,871 | B2 | 1/2005  | Patel et al. .................. 524/440 |
| 6,852,782 | B2 | 2/2005  | Patel et al. .................. 524/287 |
| 6,943,205 | B2 | 9/2005  | Patel et al. .................. 523/122 |
| 7,060,739 | B2 | 6/2006  | Patel et al. .................. 523/122 |
| 7,132,378 | B2 | 11/2006 | Kreider et al. .............. 442/177 |
| 7,182,989 | B2 | 2/2007  | Higgins et al. ................ 428/51 |
| 7,267,141 | B1 | 9/2007  | De Meyer et al. ............. 138/97 |
| 2001/0026810 | A1 | 10/2001 | McGhee et al. ............. 424/486 |
| 2006/0062831 | A1 | 3/2006  | Meyer-Ingold et al. ...... 424/443 |

FOREIGN PATENT DOCUMENTS

| DE | 10 2005 053 295 A1 | 5/2007 |
| DE | 102005053295.0 A1 | 5/2007 |
| WO | 92/04390 A1 | 3/1992 |
| WO | 9204390 A1 | 3/1992 |
| WO | 2004/007595 A1 | 1/2004 |
| WO | 2004007595 A1 | 1/2004 |

OTHER PUBLICATIONS

Anthony J. O'Lenick, Jr., "A Review of Guerbet Chemistry", *Journal of Surfactants and Detergents*, Publisher Springer Berlin / Heidelberg, pp. 1-16, vol. 4, No. 3, Jul. 2001.
Jeff Dodge, "Polyurethanes and Polyureas", *Synthetic Methods in Step-Growth Polymers*, pp. 197-263 (2003).
International Search Report for PCT/US2008/008730, mailed Sep. 5, 2008.
Guggenbichler et al., "A New Technology of Microdispersed Silver in Polyurethane Induces Antimicrobial Activity in Central Venous Catheters," *Infection*, 27 Suppl. 1, pp. S16-S23 (1999).
http://www.marubeni-sunnyvale.com/antibacterial.html, (2007) Marubeni America Corporation, Sunnyvale Office Ishizuka Glass Co. Ionpure.
http://www.antimicrobialalphasan.com/chemical/chemdivp.snf/KLWebKey/Alphasan%7E%7EWhy%20work%20with%20Mill... , (2007) Milliken Chemical AlphaSan® Processing Information.
Dodge, "Polyurethanes and Polyureas," Synthetic Methods in Step-Growth Polymers, 2003, pp. 197-263, John Wiley & Sons, Inc., Pittsburgh, Pennsylvania.
International Search Report for PCT/US2008/006730, mailed Sep. 5, 2008.

*Primary Examiner*—Kriellion A Sanders
(74) *Attorney, Agent, or Firm*—K&L Gates LLP

(57) ABSTRACT

The present invention provides novel antimicrobial polyurethane compositions having excellent mechanical and biocompatibility properties, and methods to prepare them. The antimicrobial polyurethane compositions include a homogenous distribution of silver ions by incorporating this antimicrobial agent into the composition prior to the complete polymerization of the polyurethane. In preferred embodiments, the silver ion is associated with a carrier, such as zirconium phosphate or soluble glass powder. The present invention also includes components made from the antimicrobial polyurethane compositions, such as medical devices.

35 Claims, 3 Drawing Sheets

Step A: Prepolymer formation

Step B: Polymer extension

| Antimicrobial Agents | | | Polyol | Diiso-cyanate | Diol | Catalysts | | Additives | | | | | | | |
|---|---|---|---|---|---|---|---|---|---|---|---|---|---|---|---|
| Alphasan® RC 2000 (gms) | IonPure® IPL<10μ (gms) | IonPure® IPL<40μ (gms) | PC 1122 (gms) | Desmodur W (gms) | 1,4 BDO (gms) | T-9 (gms) | K-Kat 348 (gms) | Tinuvin 765 (gms) | Irganox E201 (gms) | TNPP (gms) | Glyco-lube LV (gms) | Cab-o-sil (wt%) | Sylysia 320 (gms) | Sylysia 340 (gms) |
| 1.96 | | | 61.16 | 28.75 | 7.07 | 0.0053 | | | | | | | | |
| | | | 62.53 | 29.39 | 6.98 | 0.003 | | 0.2502 | 0.0623 | 0.2502 | 0.5005 | | | |
| 1.96 | | | 61.16 | 28.75 | 7.07 | 0.005 | | 0.2473 | 0.0603 | 0.2473 | 0.4945 | | | |
| 3.84 | | | 60.04 | 28.22 | 6.86 | 0.0097 | | 0.2427 | 0.0592 | 0.2427 | 0.4854 | | | |
| 5.59 | | | 58.93 | 27.70 | 6.75 | 0.0157 | | 0.2379 | 0.0579 | 0.2379 | 0.4765 | | | |
| 9.96 | | | 56.20 | 26.42 | 6.44 | 0.0152 | | 0.2268 | 0.0553 | 0.2268 | 0.4544 | | | |
| 8.13 | | | 57.34 | 26.96 | 6.57 | 0.0145 | | 0.2314 | 0.0564 | 0.2314 | 0.4636 | | | |
| 6.08 | | | 58.57 | 27.54 | 6.08 | 0.0438 | 0.0432 | 0.2364 | 0.0576 | 0.2364 | 0.4736 | | 1.1669 | |
| 5.54 | | | 58.44 | 27.47 | 6.35 | 0.0112 | 0.0113 | 0.2359 | 0.0575 | 0.2359 | 0.4725 | 1.1666 | | |
| 5.54 | | | 58.57 | 27.54 | 6.08 | 0.0432 | 0.0432 | 0.2364 | 0.0676 | 0.2364 | 0.4736 | | | 1.1669 |
| | 1.99 | | 61.10 | 28.76 | 6.99 | 0.0112 | 0.0115 | 0.247 | 0.0602 | 0.247 | 0.4948 | | | |
| | 1.96 | | 60.44 | 28.41 | 6.90 | 0.0185 | 0.0245 | 0.2439 | 0.0594 | 0.2439 | 0.4887 | | | 1.2041 |
| | | 1.99 | 61.25 | 28.80 | 6.88 | 0.0159 | 0.0152 | 0.2472 | 0.0602 | 0.2472 | 0.4953 | | | |
| | | 1.99 | 61.25 | 28.80 | 6.88 | 0.0159 | 0.0159 | 0.2472 | 0.0602 | 0.2472 | 0.4953 | | 0.6021 | 0.6021 |

Fig. 3

ANTIMICROBIAL POLYURETHANE RESINS AND PRODUCTS MADE THEREFROM

FIELD OF THE INVENTION

The invention relates generally to the field of antimicrobial polyurethane resin compositions and components made from them, such as medical devices.

BACKGROUND OF THE INVENTION

The incorporation of polymeric materials in the manufacture of medical devices is well established. Many invasive and non-invasive medical devices incorporating polymeric materials are used daily in the delivery of modern healthcare services. However, the wide use of polymeric materials in medical devices has been associated with an increasing incidence of patient infections. These infections are described in the medical literature as "foreign body induced infections." These infections are associated with the use of invasive polymeric-containing medical devices to penetrate the physiological skin barrier. This phenomenon is particularly common with indwelling catheters, especially when those catheters are used for extended periods.

Infections are initiated when the polymeric surface of the catheter becomes contaminated with common pathogenic skin bacteria such as *Staphylococcus aureus* and *Staphylococcus epidermidus*. The bacteria adhere to the surface of the medical device. The bacterial colonization of the polymer surface is an essential step in the pathogenesis of foreign body infections. Upon adhesion to the surface, the bacteria proliferate and produce a bio-film which is composed of the bacteria's excretion products. The bio-film encourages attachment of the pathogen and provides it with protection from attack by the patient's immune system. As the adhered pathogenic bacteria continue to proliferate, the contamination increases to a level which leads to clinical infection (septic bacterernia). The clinical protocol under this situation calls for removal of the polymeric medical device and treating the patient with both topical and systemic antibiotics.

The incidence of foreign body infections continues to increase in both acute and chronic care settings. Although it is estimated that only 5% of central venous catheters become infected, this equates to approximately 90% of all sepsis cases in intensive care medicine. The infected patients are severely compromised and secondary post treatment costs are high (approximately $25,000-$30,000 per incident).

One strategy to reduce polymeric foreign body infections is to modify the polymer by incorporating antimicrobial materials to inhibit bacterial adhesion and subsequent colonization. This in turn would reduce the chances of bacterial infection. Ideally the antimicrobial additive would be heat stable to facilitate manufacturing processes such as synthesis, extrusion and injection molding. Additionally the antimicrobial additive should be chemically non-reactive to allow for its incorporation into the resin during synthesis to obtain a high level of uniform dispersal. By incorporating the additive during polymer synthesis the requirement for a secondary compounding step is eliminated thus reducing cost and complexity. The antimicrobial additive should also be non-leaching when incorporated into the resin. This will prevent localized cellular destruction when implanted in patients, and will provide a long-lived antibacterial surface and prolonged resistance to bio-film formation and infection.

Antimicrobial agents may be broadly classified into organic and inorganic materials. Organic antimicrobial agents are often complex toxic bactericides which leach from the resin causing health concerns. Organic antimicrobial agents also include antibiotic pharmaceutical preparations which may be added to medical devices. Organic antibiotic agents are often heat labile and readily degraded by heat, humidity and mechanical processing. This makes organic antibiotic agents difficult to incorporate into many resin processing techniques.

Inorganic antimicrobial agents include metal ions, e.g. $Ag^+$, $Cu^{++}$, $Zn^{++}$. Silver ions ($Ag^+$) are preferred as they possess wide spectrum antimicrobial activity, safety and heat stability. See generally Guggenbichler et al., 1999 Infection 27 Suppl. 1, S16-S23. The broad spectrum of biocidal activity of silver ions is "oligodynamic" and includes anti-bacterial, anti-fungal and anti-viral activity. Id. The silver ions bind to sulfhydryl groups in enzyme systems and interfere with the transmembrane energy transfer and electron transport in bacterial microorganisms. Id. Silver ions also bind to the DNA of bacterial and fungi thereby increasing the stability of the bacterial double helix and inhibiting proliferation. Id. There is no microbial resistance to silver ions and no cross resistance with antibiotics. Id. The addition of silver ions directly into the resin imparts antimicrobial properties but silver discolors upon exposure to heat, humidity and light.

There are generally two broad methods for incorporating antimicrobial additives to resin systems currently in use. In first method, the antimicrobial agent is added to the finished resin by compounding or kneading the additive into the resin as a secondary processing step. This is often accomplished using melt extrusion and pelletizing equipment and requires the additive to be heat stable for extended periods. The second method involves coating the polymeric product with an agent containing the antimicrobial additive. This method results in an antimicrobial coating which, in many instances, is susceptible to mechanical damage and ultimate loss of the coating and its antimicrobial properties. Each of these methods are performed with prefabricated resin or on fabricated medical devices or device components. The incorporation of the antimicrobial agent is accomplished as one or a series of secondary steps which add cost and complexity to the manufacturing process.

There is therefore a need for a process in which an antimicrobial agent is incorporated during the synthesis of a resin suitable for molding into useful components, and in particular polyurethane for medical devices. This process should produce a resin with a homogeneous distribution of antimicrobial agent without the requirement for a secondary compounding or coating process. Further, there is a need for components that inhibit the development of bio-films. These components may be indwelling medical devices, as well as other medical devices. These components may also be those upon which undesirable biofilms form, such as in food processing, water processing, and marine equipment. The present invention addresses these needs.

SUMMARY OF THE INVENTION

The invention, in one aspect, relates to an antimicrobial polyurethane composition which includes the reaction product of a polyisocyanate, a polyol and a multihydroxyl alcohol or polyamine. At least one silver ion associated with a carrier may be added to the reaction prior to the complete polymerization. The polyisocyanate may be diisocyanate or dicyclohexlmethane diisocyanate, among others. The polyol may be polypropylene glycol, polytetramethylene glycol and their associated analogues, dihydroxyl terminated polyester, amine terminated polypropylene or polytetramethylene glycol, and in particular a polycarbonate polyol. The multihydroxyl alcohol may be a diol, a triol or 1,4 butane diol.

Additives may also be added to the antimicrobial polyurethane composition of the invention, such as antioxidants, mold release agents, color stabilizers, UV stabilizers, radiocontast agents (such as barium sulfate) and silicates. The silver ions may be associated with a carrier, such as phosphate (particularly zirconium phosphate), water soluble silicate (particularly a water soluble glass powder), zeolite, and ion exchange resin. Polyurethane resins of particular interest for making the antimicrobial polyurethane compositions of the invention are ChronoFlex® AL 80A B-20 and ChronoFlex® AL 85A.

In another aspect, the invention relates to a method of preparing an antimicrobial polyurethane composition which includes the steps of reacting a polyisocyanate and a polyol to produce a prepolymer, and reacting the prepolymer with a multihydroxyl alcohol or polyamine to produce the polyurethane composition. At least one silver ion associated with a carrier may be added to the reaction prior to complete polymerization. The polyisocyanate used in this method may be diisocyanate or dicyclohexylmethane diisocyanate. The polyol may be polypropylene glycol, polytetramethylene glycol and their associated analogues, dihydroxyl terminated polyester, amine terminated polypropylene, polytetramethylene glycol or polycarbonate polyol. The multihydroxyl alcohol may be a diol, a triol and 1,4 butane diol. The carrier associated with the silver ion may be a phosphate (such as zirconium phosphate), a soluble silicate (such as a water soluble glass powder), a zeolite, or an ion exchange resin.

The method to prepare a antimicrobial polyurethane composition may also have the step of adding micronized silica and/or barium sulfate. The method may use the ingredients found in Tables 1 or 2 to make the antimicrobial polyurethanes. The silver ion with carrier may be added prior to or after prepolymer formation. Finally, the method may include the addition of an appropriate catalyst.

In yet another aspect, the invention relates to a method for making an antimicrobial polyurethane component including the steps of reacting a polyisocyanate and a polyol to produce a prepolymer, reacting a multihydroxyl alcohol and the prepolymer to produce a polyurethane composition. At least one silver ion associated with a carrier may be added to the reaction prior to complete polymerization. The method further includes the steps of curing the polyurethane composition, forming pellets from the polyurethane composition, and forming the polyurethane component from the pellets.

In yet another aspect, the invention relates to components made from the antimicrobial polyurethane compositions of the invention. Components made from the antimicrobial components of the invention include medical devices.

DESCRIPTION OF THE DRAWINGS

The invention is pointed out with particularity in the appended claims. The advantages of the invention described herein, together with further advantages, may be better understood by referring to the following description taken in conjunction with the accompanying figures.

FIG. 3 is a table of various polyurethane formulations prepared using traditional polyols, diisocyanates, and alcohol and amine-based chain extenders, and antimicrobial agents and other additives. Alphasan® RC 2000 (Milliken and Co., Spartanburg, S.C.) is a zirconium phosphate-based silver ion-containing ion exchange resin. IonPure® IPL<10μ (Ishizuka Glass Co., Naguya, Japan) is a composition of soluble glass particles (less than 10 microns) which contain silver ions. IonPure® IPL<40μ (Ishizuka Glass Co., Naguya, Japan) is a composition of soluble glass particles (less than 40 microns) which contain silver ions. PC-1122 (Stahl U.S.A., Peabody, Mass.) is a polycarbonate polyol. Desmodur® W (Bayer MaterialScience LLC, Pittsburgh Pa.) is dicyclohexylmethane diisocyanate. T-9 or Dabco® T-9 (Air Products and Chemicals Inc., Allentown, Pa.) is stannous octoate. K-Kat® 348 (King Industries, Inc., Norwalk Conn.) is bismuth carboxylate. Tinuvin® 765 (Ciba Specialty Chemicals, Tarrytown N.Y.) is an antioxidant. Irganox® E-201 (Ciba Specialty Chemicals, Tarrytown N.Y.) is Vitamin E. TNPP is tris(nonylphenyl)phosphite. Glycolube® LV (Lonza Inc., Allendale N.J.) is a lubricant wax. CAB-O-SIL® TS-720 (Cabot Corp., Alpharetta, Ga.) is fumed silica. Sylysia® 320 and Sylysia® 340; where 320 and 340 refer to particle size (Fuji Silysia Chemical Ltd., Aichi Japan) are micronized silica.

DETAILED DESCRIPTION OF THE INVENTION

The present invention provides novel polyurethane resin compositions having excellent mechanical, biocompatibility and antimicrobial properties. In many embodiments, the polyurethane resins include a homogenous distribution of an antimicrobial agent by incorporating antimicrobial agent into the resin prior to the complete polymerization of the polyurethane. In preferred embodiments, the antimicrobial agent is silver, and may be associated with a carrier. The silver may, for example, be an ion associated with a phosphate or a water soluble glass powder. Further, the present invention includes methods by which these antimicrobial polyurethane resins may be made, and methods to make useful components from the antimicrobial polyurethane resins of the invention. Finally, the present invention includes the components made from these antimicrobial polyurethane resins.

Figure 1:
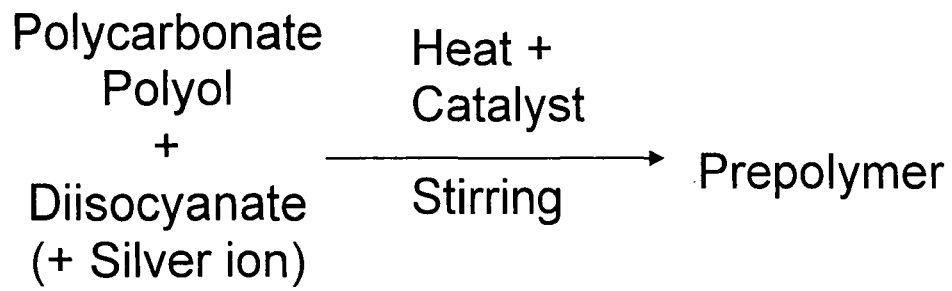
FIG. 1 is a diagram of an embodiment of the method for preparing an antimicrobial polyurethane composition of the invention.
Figure 1:
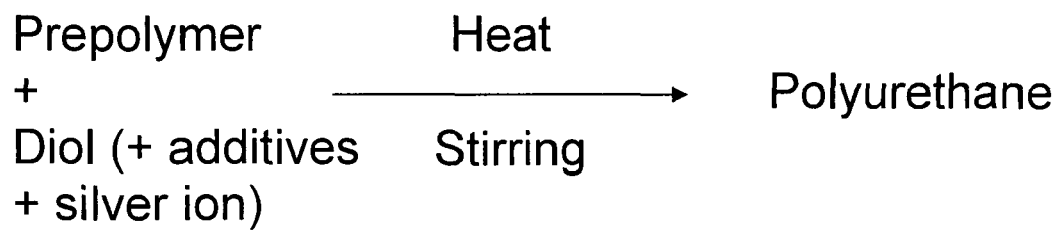
Figure 2:
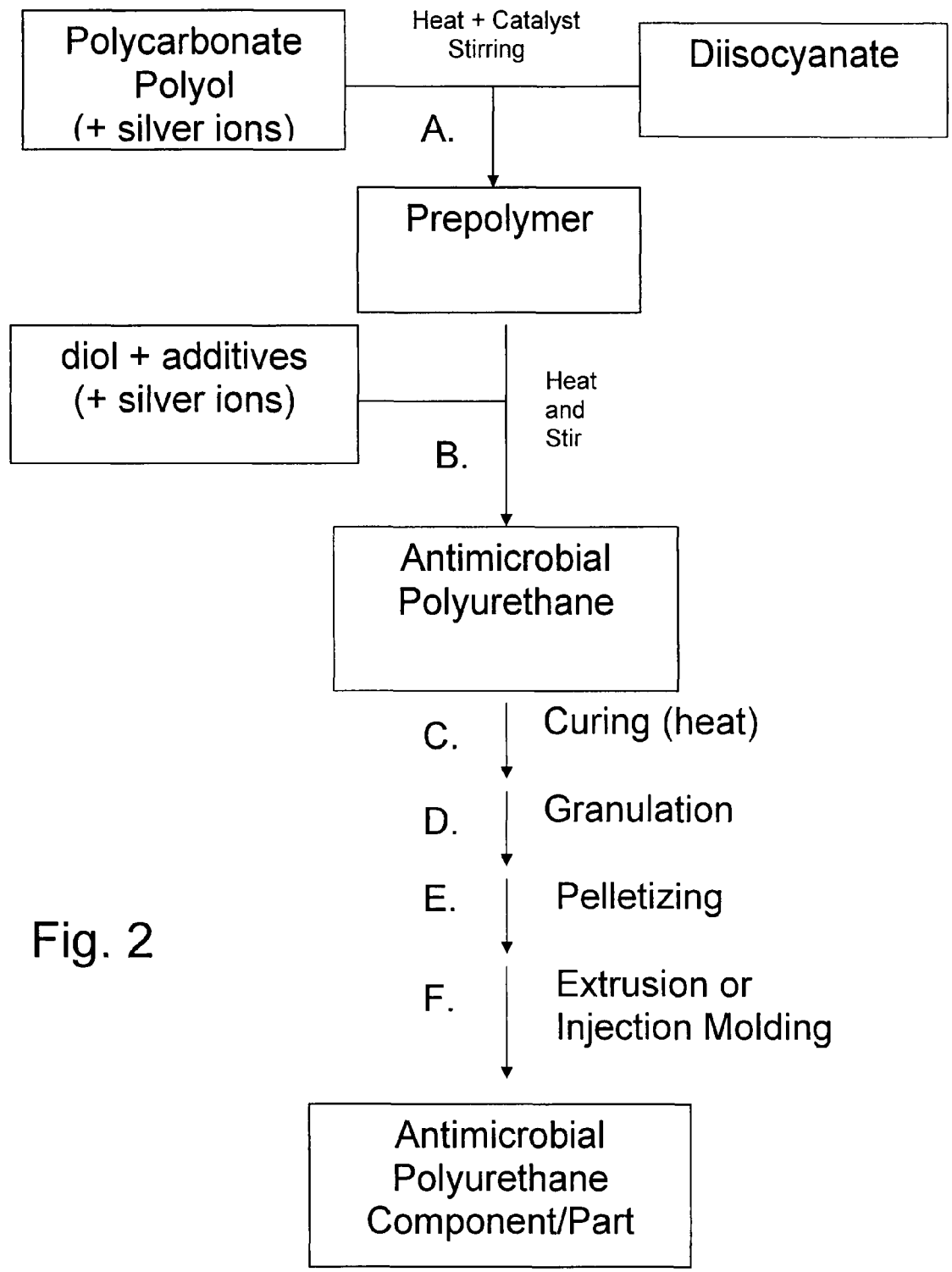
FIG. 2 is a flow diagram of an embodiment of a method for making an antimicrobial polyurethane component of the invention. The letters "A" through "F" refer to steps A through F.

The antimicrobial polyurethane compositions of the invention include the product of the reaction of a polyisocyanate, a polyol and a multihydroxyl alcohol or polyamine with an antimicrobial agent. The antimicrobial agent in one embodiment is at least one silver ion associated with a carrier which is added to the reaction prior to the completion of the polyurethane polymerization. The antimicrobial polyurethane compositions of the invention may be prepared by reacting a polyisocyanate and a polyol to produce a prepolymer, reacting the prepolymer and a multihydroxyl alcohol or polyamine to produce the polyurethane composition; and adding at least one silver ion associated with a carrier to the reaction prior to complete polymerization of the polyurethane. See FIG. 1. Finally, antimicrobial polyurethane components may be prepared according to the method of the invention by preparing the antimicrobial polyurethane as described above, with the additional steps of curing the antimicrobial polyurethane composition, forming pellets of the antimicrobial polyurethane composition, and forming the antimicrobial polyurethane component from the pellets. In both the methods to make the antimicrobial polyurethane and the methods to make the antimicrobial polyurethane components, more than one step may be performed simultaneously. See FIG. 2. In some embodiments, the step of producing the prepolymer is performed simultaneously with the formation of the final polyurethane resin and the addition of the silver ion associated with a carrier. See FIG. 1 and FIG. 2.

The polyurethane resin may be any one of many formulations currently known, the composition and method of making both will be well known to those of ordinary skill in the art. Such polyurethane resins are preferably solid when completely polymerized, however polyurethane resins of differing viscosities are contemplated to be within the scope of the invention. In some embodiments, the polyurethane may be a polyurethane foam, or a liquid composition of polyurethane than can be used to coat components. Depending on the ultimate use of the antimicrobial polyurethane, a polyurethane resin formulation may be chosen to provide important physical and chemical characteristics for that application. For example, antimicrobial polyurethane resins to be used for medical devices may be those which are biostable. Other characteristics of importance include, but are not limited to, elasticity, and tensile strength. To further illustrate but not limit the invention, a polyurethane resin particularly suitable to be used to form a vascular graft may have high tensile strength and a low elastic modulus. Preferred polyurethane formulations are described in U.S. Pat. No. 5,863,627 entitled "Hydrolytically and Proteolytically Stable Polycarbonate Silicone Copolymers," and U.S. Pat. No. 5,254,662 entitled "Biostable Polyurethane Products." Both of these patents are incorporated herein by reference. Other preferred polyurethane resin formulations useful in making the include the ChronoFlex® polyurethane resins (Cardiotech International Inc., Wilmington, Mass.), and in particular ChronoFlex® AL 85A and ChronoFlex® AL 80A B-20 (see Tables 1 and 2).

TABLE 1

Composition of ChronoFlex ® AL 85A.

| INGREDIENTS | EQ WT | WEIGHT | PERCENT |
|---|---|---|---|
| PC-1122 | 935.00 | 542.30 | 61.48 |
| 1,4 Butane Diol | 45.05 | 63.97 | 7.25 |
| Glycolube ® VL | | | 0.25 |
| Tinuvin ® 765 | | | 0.20 |
| TNPP | | | 0.20 |
| Irganox ® E 201 | | | 0.05 |
| Dabco ® T-9 | | | 0.034 |
| Subtotal | | 606.27 | 69.47 |
| Desmodur ® W | 132.00 | 269.28 | 30.53 |
| TOTAL | | 875.55 | 100.00 |

TABLE 2

Composition of ChronoFlex ® AL 80A B-20.

| INGREDIENTS | EQ WT | WEIGHT | PERCENT |
|---|---|---|---|
| PC-1122 | 935.00 | 578.77 | 50.20 |
| Butanediol | 45.05 | 62.17 | 5.39 |
| Barium Sulfate | | | 20.00 |
| Tinuvin ® 765 | | | 0.20 |
| TNPP | | | 0.20 |
| Glycolube ® VL | | | 0.50 |
| Stannous Octoate | | | 0.03 |
| Ronotec ® 201 | | | 0.05 |
| Subtotal | | 640.93 | 76.57 |
| Desmodur ® W | 132.00 | 270.10 | 23.43 |
| TOTAL | | 911.03 | 100.00 |

The carrier associated with the silver ion in these polyurethane resins is, in some embodiments, one which protects the silver ion from discoloration when exposed to heat, humidity and/or light. Carriers of particularly interest include zeolite, phosphates and soluble silicates, among others. In one preferred embodiment, the silver ion carrier is a zirconium phosphate, such as but not limited to Alphasan® RC 2000 (Milliken and Co., Spartanburg, S.C.). In another preferred embodiment, the silver ion carrier is a soluble silicate, preferably one that is soluble in water, such as, but not limited to, IonPure® IPL<10µ or IonPure® IPL<40µ (Ishizuka Glass Co., Naguya, Japan). The soluble silicate may be a glass powder, such as sodium silicate, but may also be another form of silicate such as, but not limited to, a potassium silicate. In some embodiments, the soluble silicate is soluble in an aqueous environment. The preferred method of synthesis is a polymerization performed with the reactants in a molten form, however, the antimicrobial polyurethanes of the invention may also be made in solution, such as in the solvent dimethylacetamide. The silver ion may be associated with the carrier by one or more of many well-known physical and chemical means. In some embodiments, the association of the silver with the carrier is by ionic bonds, covalent bonds, and/or physical sequestration. In preferred embodiments, the antimicrobial polyurethane composition includes at least about 0.1%, 0.5%, 1.0% or 2.0% silver ion on a weight basis. In some embodiments, the antimicrobial polyurethane composition includes at least about 1.0%, 2.0%, 4.0%, 6.0%, 8.0% or 10.0% of the silver ion associated with soluble silica on a weight basis. In some embodiments, the antimicrobial polyurethane composition includes at least about 2.0%, 4.0%, 6.0%, 8.0% or 10.0% of the silver ion associated with zirconium phosphate on a weight basis.

The antimicrobial polyurethane compositions, and components made from them, may have many advantageous properties. These antimicrobial polyurethane compositions may have a low to zero level of leaching of the incorporated silver ions. In preferred embodiments, the antimicrobial polyurethane compositions show no zone of inhibition in the Kirby-Bauer Susceptibility Test. In other embodiments, the antimicrobial polyurethane compositions show a high bacterial "kill" across a wide spectrum of bacteria, including both gram positive and gram negative bacteria. The bacterial "kill" of the composition is most preferably measured by the American Association of Textile Chemists and Colorists (AATCC) Method 100 (Modified). In some embodiments, the antimicrobial polyurethane composition kills *Staphylococcus epidermidis* and/or *Pseudomonas aeruginosa* with at least about 50%, 70%, 90%, 95% or 99% reduction in colony forming units (CFU) after 24 hours contact time using the AATCC Method 100 (Modified) test. In other embodiments, the antimicrobial polyurethane has a hardness when measured by a durometer of at least about 70, 80, 85 or 90 Shore A.

In accordance with the invention, it has been discovered that specific combinations of polyurethane resin formulations, antimicrobial agents and micronized silica provide antimicrobial polyurethanes that are surprisingly effective in killing surface bacteria. Specifically, it has been discovered that combinations of Chronoflex® AL 85A with zirconium phosphate-based silver ion (Alphasan® RC2000) and micronized silica (such as Sylysia® 320), and with soluble glass particles with silver ions (IonPure®) and micronized silica (such as Sylysia® 340) are particularly effective wide spectrum antimicrobial polyurethane compositions. Surprisingly, it has been additionally discovered that Chronoflex® AL 80A B-20, or polyurethane with barium sulfate, when combined with zirconium phosphate-based silver ion (Alphasan® RC2000) or soluble glass particles with silver ions (IonPure®) makes a particularly effective wide spectrum antimicrobial polyurethane composition.

In preferred embodiments, the antimicrobial polyurethane composition kills both gram positive and gram negative bacteria, and specifically *Staphylococcus epidermidis* and *Pseudomonas aeruginosa*. In particularly preferred embodiments, the antimicrobial polyurethane composition kills both gram positive and gram negative with at least about 99% reduction in CFU after 24 hours contact time using the AATCC Method 100 (modified). One particularly preferred embodiment the antimicrobial polyurethane includes Chronoflex® AL 85A with 5.56% Alphasan® RC2000 and 1.2% Sylysia 320. In another preferred embodiment, the antimicrobial polyurethane includes Chronoflex® AL 85A with 2% IonPure® and 1.2% Sylysia® 340. In another preferred embodiment, the antimicrobial polyurethane includes Chronoflex® AL 80A B-20, or another polyurethane resin with barium sulfate with 2% IonPure®. In yet another preferred embodiment, the antimicrobial polyurethane includes Chronoflex® AL 80A B-20, or another polyurethane resin with barium sulfate, with 6% Alphasan® RC2000. In some preferred embodiments, the polyurethane resin includes at least about 5%, 10%, 15%, 20% or 25% barium sulfate. In other preferred embodiments, at least about 0.6% 1.2%, 1.8% or 2.4% Sylysia® or other micronized silica is added to the antimicrobial polyurethane resin.

The polyisocyanate which is used in the methods to prepare antimicrobial compositions and components may be any polyisocyanate which is at least a diisocyanate. Polyisocyanate selection should be made with due consideration to the viscosity of the molten mixture in the prepolymer polymerization step as a higher viscosity molten mix will hinder the dispersal of the silver-containing additive. In a preferred embodiments, the polyisocyanate is represented by the formula OCN—R—NCO wherein R is aliphatic, including groups such as aliphatic, aliphatic-alicyclic and aliphatic-aromatic hydrocarbon groups containing from about 4 to 26 carbon atoms, preferably from about 6 to 20 carbon atoms, more preferably from about 6 to 13 carbon atoms or an aromatic group preferably carbocyclic aryl or aralkyl having from about 6 to 14 carbon atoms. Representative examples of such diisocyanates include: tetramethylene diisocyanate, hexamethylene diisocyanate, trimethylhexamethylenediisocyanate, tetramethylxylylene diisocyanate, 4,4-dicyclohexylmethane diisocyanate, dimer acid diisocyanate, isophorone diisocyanate, metaxylene diisocyanate, diethylbenzene diisocyanate, decamethylene 1,10-diisocyanate, cyclohexylene 1,2-diisocyanate and cyclohexylene 1,4-diisocyanate, 2,4-toluene diisocyanate; 2,6-toluene diisocyanate; xylene diisocyanate; m-phenylene diisocyanate; hexahydrotolylene diisocyanate (and isomers), naphthylene-1,5-diisocyanate; 1-methoxyphenyl 2,4-diisocyanate diphenylmethane 4,4'-diisocyanate, 4,4'-biphenylene diisocyanate, 3,3-dimethoxy-4,4-biphenyldiisocyanate; 3,3-dimethyl 4,4'-diisocyanate and mixtures thereof. In a particularly preferred embodiment, the polyisocyanate is dicyclohexylmethane diisocyanate, such as Desmodur® W (Bayer MaterialScience LLC, Pittsburgh Pa.).

The polyol which is used in the methods to prepare antimicrobial compositions and components may advantageously be a polycarbonate polyol, which are more stable than traditional polyols when implanted in the human body. Polycarbonate glycols useful in making the present polyurethanes may have molecular weight of from about 650 to 3500 molecular weight units, preferably 1000 to 2000 molecular weight units and may have the following formula

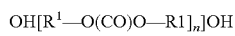

OH[R$^1$—O(CO)O—R1]$_n$OH in which R$^1$ is a linear chain of about 2 to 20 carbon atoms. A preferred polycarbonate glycol is hexanediolcarbonate glycol. Traditional polyols are also contemplated to be within the scope of the invention. Traditional polyols include, but are not limited to, polypropylene glycol, polytetramethylene glycol and their associated analogues, dihydroxyl terminated polyester, amine-terminated polypropylenes and polytetramethylene glycols.

The multihydroxyl alcohol used in chain extension step in the methods to prepare antimicrobial compositions and components may advantageously be a diol. Triol and higher multihydroxyl analogues are also contemplated to be within the scope of the invention, such as glycine. The diols chain extenders which are useful the present invention may have from about 2 to 8 carbon atoms which are preferably in a straight chain with no more than 2 side groups, such as methyl or ethyl. Exemplary of these diols are ethylene glycol, diethylene glycol, triethylene glycol, 1,4-butane diol, neopentyl glycol, 1,6-hexanediol, 1,8-octane diol, 1,2 and 1,3-propylene glycol, 2,3-butylene glycol, dipropylene glycol, dibutylene glycol and mixtures thereof. Preferably the multihydroxyl alcohol used for chain extension is 1,4 butane diol.

Additionally, polyamines such as diamines may also be used in the chain extension reaction. Polyamines may be used to form highly branched polyurethanes. Suitable aliphatic diamine chain extenders include diamines which may have about 2 to 10 carbon atoms. Exemplary diamines include ethylene diamine, propanediamines, butanediamine, pentanediamine, hexanediamine, heptanediamine, octanediamine, m-xylylene diamine, 1,4-diaminocyclohexane, 2-methylpentamethylene diamine and mixtures thereof. Suitable alkanolamine chain extenders include ethanolamine and the like.

Chemical additives may be added during the polymerization reactions in the methods to prepare antimicrobial polyurethane compositions and components in order to give the resulting compositions additional properties, such as to aid the downstream processing. Many such chemical additives are traditionally used in the preparation of polyurethanes and will be know to those of ordinary skill in the art. Chemical additives of interest include, but are not limited to, antioxidants, mold release agents, color stabilizers, and UV stabilizers. Chemical additives of particular interest include Tinuvin® 765 (Ciba Specialty Chemicals, Tarrytown N.Y.), Irganox® E-201 (Ciba Specialty Chemicals, Tarrytown N.Y.), tris(nonylphenyl)phosphite (TNPP), Glycolube® LV (Lonza Inc., Allendale N.J.), and CAB-O-SIL® TS-720 (Cabot Corp., Alpharetta, Ga.). In some embodiments, the chemical additive enhances the antimicrobial activity of the silver ion, such as micronized silica (Sylysia® 320 or 340, 320/340 refering to particle size (Fuji Silysia Chemical Ltd., Aichi Japan). Preferably, the chemical additives are added during the polymer chain extension step. See FIG. 1. Suitable concentrations of the chemical additives will be know to those of ordinary skill in the art, and exemplary concentrations are found in FIG. 3.

One or more catalysts may be added during the polymerization reactions in the methods to prepare antimicrobial polyurethane compositions and components. These catalysts are most advantageously added during the prepolymer formation step, but may be added at any time during the polyurethane polymerization, particularly when prepolymer formation and polymer chain extension are undertaken simultaneously. See FIG. 1. Conventional polyurethane catalysts such as organometallic compounds may be employed. Illustrative such catalysts are dibutyl tin dilaurate, dioctyl tin diluarate, stannous octoate and zinc octoate. In preferred embodiments, the catalysts stannous octoate (T-9, Air Products and Chemicals Inc., Allentown, Pa.) and/or bismuth carboxylate (K-Kate 348, King Industries, Inc., Norwalk Conn.) may be used, either singly or in combination with each other or other catalysts. These catalysts may be used in concentrations similar to those disclosed in FIG. 3 or in Tables 1 and 2. In preferred embodiments, the prepolymer formation step and/or the polymer extension steps are performed at elevated temperatures, as well be know to those of ordinary skill in the art.

Components useful in many diverse applications may be made with the antimicrobial polyurethane compositions presented herein. Medical devices are particularly of interest, especially where the medical device will be invasive. An "invasive medical device" as used herein, is one that will be located partially or completely within the body of the patient. An "invasive medical device" may be inserted into or under the skin or the body cavity; for example, catheters and stent grafts. In some cases, an "invasive medical device" will be inserted into an orifice of the body, but not into the body cavity itself; for example, urinary drainage devices and ventilators. Indwelling medical devices that remain for long periods of time in the body of the patient are of particular interest. Medical devices of particular interest include, but are not limited to, vascular grafts, pacemaker leads, mammary prostheses, probes, cannulas and catheters. Non-invasive medical devices include ocular devices and dental devices. Other applications that may benefit from the antimicrobial properties of the polyurethanes of the invention, particularly those that have a problematic formation of bio-films. Other applications of interest include components for the food service industry, textile manufacture, paper manufacture, plumbing, oil recovery, waste water processing, and marine equipment.

The antimicrobial polyurethane components of the invention may be prepared by any method that forms the antimicrobial polyurethane into a useful component. Many such methods are known in the art. In some situations, the antimicrobial polyurethane may be spread or sprayed onto a component, such as when the antimicrobial is a varnish or a foam. In some embodiments, the antimicrobial polyurethane is "cured" before forming the component, preferably by heating. See FIG. 2. To facilitate the formation process, the antimicrobial polyurethane may be pelletized, according the processes well know in the industry. Upon pelletization, additives may be introduced into the polyurethane compositions. In other embodiments, the antimicrobial polyurethane is formed into the desired component by extrusion or injection molding, which may be performed using standard industry equipment.

Example

Various polyurethane formulations were prepared using traditional polyols, diisocyanates, and alcohol and amine-based chain extenders. See FIG. 3. During the reaction sequence of these polyurethanes, varying quantities of a zirconium phosphate-based silver ion-containing ion exchange resin (Alphasan® RC 2000, Milliken and Co., Spartanburg, S.C.) or alternately varying quantities of water-soluble glass particles containing silver ions (IonPure® IPL, Ishizuka Glass Co., Naguya, Japan) were added to the reaction mixtures and entrapped in the polymer structure during the polyurethane polymerization. Various additives were included in the formulations to enhance the polymer's physical and processing characteristics and to optimize the resulting polymers antimicrobial properties.

A selection of the antimicrobial polyurethanes synthesized were tested by two separate bacteriological testing protocols to determine their ability to "kill" bacterial challenges. The two testing methods used were:

Kirby-Bauer Susceptibility Test (zone of inhibition development)

AATCC Method 100 (Modified)

The bacterial challenges used were:

*Staphylococcus epidermidis*, ATCC No. 12228

*Psuedomonas aeruginosa*, ATCC No. 9027

Kirby-Bauer Susceptibility Test looks for the development of a zone of inhibition (indicative of the inhibition of bacterial growth) under and surrounding the test sample. Bauer, A. W. et al, Antibiotic Susptibility Testing by Standardized Single Disk Method, Am. J. Clin. Pathol., 1966, 45(4): 493-496. The formation of a zone of inhibition indicates that the antimicrobial agent is leaching from the test sample and killing bacteria (and other cells) in the zone of inhibition.

Polyurethane samples (ChronoFlex® AL 85A, Cardiotech International Inc., Wilmington, Mass.) containing various levels (0%-10%) of zirconium phosphate-based silver ion-containing ion exchange resin (Alphasan® RC 2000) were tested using the Kirby-Bauer protocol. See Table 3. The results indicated that none of the antimicrobial polyurethane samples tested formed a zone of inhibition. This indicated that the antimicrobial agent present in the polyurethane samples tested was non-leaching. This non-leaching property reduces the risk of collateral cell death when these materials are used to fabricate implantable medical devices.

TABLE 3

The degree of formation of a zone of inhibition on selected antimicrobial polyurethane resins as determine by the Kirby-Bauer Susceptibility Test.

| Polymer Description | Sample ID | Alphasan ® RC 2000 Concentration (weight %) | Organism | Zone of Inhibition |
| --- | --- | --- | --- | --- |
| CF 85A | 1 | 0 | Staphylococcus epidermidis | NZ/NC |
| CF 85A w/ 2% Alphasan ® RC2000 | 2 | 2 | Staphylococcus epidermidis | NZ/NC |
| CF 85A w/ 4% Alphasan ® RC2000 | 3 | 4 | Staphylococcus epidermidis | NZ/NC |
| CF 85A w/ 6% Alphasan ® RC2000 | 4 | 6 | Staphylococcus epidermidis | NZ/NC |
| CF 85A w/ 10% Alphasan ® RC2000 | 5 | 10 | Staphylococcus epidermidis | NZ/NC |
| CF 85A | 1 | 0 | Pseudomonas aeruginosa | NZ/NC |
| CF 85A w/ 2% Alphasan ® RC2000 | 2 | 2 | Pseudomonas aeruginosa | NZ/NC |
| CF 85A w/ 4% Alphasan ® RC2000 | 3 | 4 | Pseudomonas aeruginosa | NZ/NC |
| CF 85A w/ 6% Alphasan ® RC2000 | 4 | 6 | Pseudomonas aeruginosa | NZ/NC |

TABLE 3-continued

The degree of formation of a zone of inhibition on selected antimicrobial polyurethane resins as determine by the Kirby-Bauer Susceptibility Test.

| Polymer Description | Sample ID | Alphasan ® RC 2000 Concentration (weight %) | Organism | Zone of Inhibition |
|---|---|---|---|---|
| CF 85A w/ 10% Alphasan ® RC2000 | 5 | 10 | *Pseudomonas aeruginosa* | NZ/NC |

"NZ/NC" indicates that no zone of inhibition was seen/no clearing of growth underneath sample.
"CF" indicates Chronoflex ® AL polyurethane resin (CardioTech International, Inc., Wilmington, MA).

A second series of polyurethane samples, some containing zirconium phosphate-based silver ion-containing ion exchange resin (Alphasan® RC 2000, Milliken and Co., Spartanburg, S.C.) while others containing silver ion-containing soluble glass particles (IonPure® IPL, Ishizuka Glass Co., Naguya, Japan), where subjected to the AATCC Method 100 (modified) bacteriological testing protocol. The AATCC 100 (modified) testing protocol is used to determine the antimicrobial characteristics of non-fugitive antimicrobial agents. The term "non-fugitive," as used herein, is used to describe the nature of the antimicrobial agent in the polyurethane composition, which, barring exposure of the polyurethane polymer itself to severe conditions of hydrolysis or decomposition, cannot be eliminated from the polyurethane composition. The AATCC 100 (modified) testing protocol has found particular utility in the testing of antimicrobial textile fibers. Various additives were included in the formulations to enhance the polymer's physical and processing characteristics and to optimize the resulting polymers antimicrobial properties. Sylysia® 320 and Sylysia® 340 (Fuji Sylysia Chemical Ltd., Aichi Japan) are micronized silica.

Antimicrobial polyurethane polymer compositions of the present invention showed high bacterial "kill" across a broad spectrum of polymer compositions and bacterial types (both gram positive and negative) when tested by the AATCC 100 (modified) method. This method is quantitative in nature and provides data on the percentage "kill" a particular antimicrobial structure provides. See Table 4. The results indicated that the majority of formulations exhibit a high level of "kill" (>99% in many instances) for both bacterial challenges (gram positive and negative).

TABLE 4

Bacterial "kill" of selected antimicrobial polyurethane compositions as determined by the AATCC 100 (modified) method.

| Polymer Description | Organism | Initial Contact Time (CFU/sample) | 24 Hour Contact Time (CFU/sample) | Percent Reduction (%) |
|---|---|---|---|---|
| CF 85A w/ 6% Alphasan ® RC2000 | *Staphylococcus epidermidis* | $2.0 \times 10^5$ | $8.5 \times 10^2$ | 99.58 |
| CF 85A w/ 5.56% Alphasan ® RC2000/ 1.2% Sylysia 320 | *Staphylococcus epidermidis* | $1.7 \times 10^5$ | $8.0 \times 10^2$ | 99.53 |
| CF 85A w/ 2% IonPure ® | *Staphylococcus epidermidis* | $1.7 \times 10^5$ | $8.1 \times 10^4$ | 52.35 |
| CF 85A w/ 2% IonPure ®/1.2% Sylysia ® 340 | *Staphylococcus epidermidis* | $1.6 \times 10^5$ | $2.0 \times 10^2$ | 99.88 |
| CF 85A w/ 2% IonPure ®/ 0.6%/0.6% Sylysia ® 320/340 | *Staphylococcus epidermidis* | $1.7 \times 10^5$ | $2.6 \times 10^3$ | 98.47 |
| CF 80A B-20 w/ 2% IonPure ® | *Staphylococcus epidermidis* | $1.4 \times 10^5$ | $<1.0 \times 10^2$ | >99.93 |
| CF 80A B-20 w/ 6% Alphasan ® RC2000 | *Staphylococcus epidermidis* | $1.7 \times 10^5$ | $<1.0 \times 10^2$ | >99.4 |
| CF 85A w/ 6% Alphasan ® RC2000 | *Pseudomonas aeruginosa* | $1.3 \times 10^5$ | $1.7 \times 10^5$ | NR |
| CF 85A w/ 5.56% Alphasan ® RC2000/ 1.2% Sylysia ® 320 | *Pseudomonas aeruginosa* | $1.4 \times 10^5$ | $2.5 \times 10^2$ | 99.82 |
| CF 85A w/ 2% IonPure ® | *Pseudomonas aeruginosa* | $1.2 \times 10^5$ | $<1.0 \times 10^2$ | >99.92 |
| CF 85A w/ 2% IonPure ®/1.2% Sylysia 340 | *Pseudomonas aeruginosa* | $1.3 \times 10^5$ | $1.3 \times 10^3$ | 99.00 |
| CF 85A w/ 2% IonPure ®/ 0.6%/0.6% Sylysia ® 320/340 | *Pseudomonas aeruginosa* | $1.4 \times 10^5$ | $2.7 \times 10^7$ | NR |

TABLE 4-continued

Bacterial "kill" of selected antimicrobial polyurethane compositions as determined by the AATCC 100 (modified) method.

| Polymer Description | Organism | Initial Contact Time (CFU/sample) | 24 Hour Contact Time (CFU/sample) | Percent Reduction (%) |
|---|---|---|---|---|
| CF 80A B-20 w/ 2% IonPure ® | *Pseudomonas aeruginosa* | $1.1 \times 10^5$ | $<1.0 \times 10^2$ | >99.91 |
| CF 80A B-20 w/ 6% Alphasan ® RC2000 | *Pseudomonas aeruginosa* | $1.4 \times 10^5$ | $<1.0 \times 10^2$ | >99.93 |

"CF" refers to ChromoFlex ® AL polyurethane resin (CardioTech International, Inc., Wilmington, MA).

Further physical testing was performed on selected sample formulations of antimicrobial polyurethanes to determine the effect of the quantity of antimicrobial additive on the hardness of the material. Antimicrobial polyurethane formulations with 0% to 10% zirconium phosphate-based silver ion-containing ion exchange resin were fabricated into samples sufficient to determine the materials hardness (durometer) as a function of antimicrobial agent content. The results showed a modest reduction in hardness with increasing antimicrobial additive content. See Table 5.

TABLE 5

Polymer hardness as a function of antimicrobial additive concentration.

| Polymer | Alphasan ® Concentration | Durometer (Shore A) |
|---|---|---|
| CF AL 85A Control | 0 | 90 |
| CF AL 85A 2% Alphasan ® | 2 | 90 |
| CF AL 85A 4% Alphasan ® | 4 | 87 |
| CF AL 85A 6% Alphasan ® | 6 | 85 |
| CF AL 85A 8% Alphasan ® | 8 | 83 |
| CF AL 85A 10% Alphasan ® | 10 | 82 |

"CF" refers to ChromoFlex ®.

While the present invention has been described in terms of certain exemplary preferred embodiments, it will be readily understood and appreciated by one of ordinary skill in the art that it is not so limited, and that many additions, deletions and modifications to the preferred embodiments may be made within the scope of the invention as hereinafter claimed. Accordingly, the scope of the invention is limited only by the scope of the appended claims.

The invention claimed is:

1. An antimicrobial polyurethane composition comprising a reaction product of
   a polyisocyanate,
   a polycarbonate polyol, and
   a multihydroxyl alcohol or polyamine,
   wherein at least one silver ion associated with a carrier is added to the reaction product prior to complete polymerization; and
   wherein the polymerized antimicrobial polyurethane composition exhibits substantially no leaching of silver ions as shown by the lack of formation of a zone of inhibition in a Kirby-Bauer test.

2. The antimicrobial polyurethane composition of claim 1, wherein the polyisocyanate is a diisocyanate, the multihydroxyl alcohol is a diol or a triol, and the polyamine is a diamine.

3. The antimicrobial polyurethane composition of claim 1, wherein:
   the polyisocyanate is selected from the group consisting of tetramethylene diisocyanate, hexamethylene diisocyanate, trimethylhexamethylenediisocyanate, tetramethylxylylene diisocyanate, dicyclohexylmethane diisocyanate, isophorone diisocyanate, diethylbenzene diisocyanate, decamethylene 1,10-diisocyanate, cyclohexylene 1,2-diisocyanate, cyclohexylene 1,4-diisocyanate, 2,4-toluene diisocyanate, 2,6-toluene diisocyanate, xylene diisocyanate, m-phenylene diisocyanate, hexahydrotolylene diisocyanate, naphthylene-1,5-diisocyanate, 1-methoxyphenyl 2,4-diisocyanate, diphenylmethane 4,4'-diisocyanate, 4,4'-biphenylene diisocyanate, 3,3-dimethoxy-4,4-biphenyldiisocyanate, 3,3-dimethyl 4,4'-diisocyanate, and mixtures thereof;
   the multihydroxyl alcohol is selected from the group consisting of ethylene glycol, diethylene glycol, triethylene glycol, 1,4-butane diol, neopentyl glycol, 1,6-hexanediol, 1,8-octane diol, 1,2-propylene glycol, 1,3-propylene glycol, 2,3-butylene glycol, dipropylene glycol, dibutylene glycol, and mixtures thereof; and
   the polyamine is selected from the group consisting of ethylene diamine, propanediamine, butanediamine, pentanediamine, hexanediamine, heptanediamine, octanediamine, m-xylylene diamine, 1,4-diaminocyclohexane, 2-methylpentamethylene diamine, and mixtures thereof.

4. The antimicrobial polyurethane composition of claim 1, which additionally comprises one or more additives selected from the group consisting of an antioxidant, a mold release agent, a color stabilizer, a UV stabilizer and a silicate.

5. The antimicrobial polyurethane composition of claim 1, wherein the carrier associated with the silver ion is one or more selected from the group consisting of a phosphate, a soluble silicate, a zeolite, and an ion exchange resin.

6. The antimicrobial polyurethane composition of claim 5, wherein the carrier associated with the silver ion is zirconium phosphate.

7. The antimicrobial polyurethane composition of claim 6, which further comprises at least one component selected from the group of micronized silica and barium sulfate.

8. The antimicrobial polyurethane composition of claim 6, comprising a polycarbonate polyurethane CHRONOFLEX® AL 80A B-20, which comprises a reaction product of dicyclohexylmethane diisocyanate, a polycarbonate diol, and 1,4-butane diol.

9. The antimicrobial polyurethane composition of claim 5, which further comprises at least one component selected from the group of micronized silica and barium sulfate, and wherein the carrier associated with the silver ion is a water soluble glass powder.

10. The antimicrobial polyurethane composition of claim 1, comprising a polycarbonate polyurethane CHRONOFLEX® AL 85A or CHRONOFLEX® AL 80A B-20, each of which comprises a reaction product of dicyclohexylmethane diisocyanate, a polycarbonate diol, and 1,4-butane diol.

11. The antimicrobial polyurethane composition of claim 9, comprising a polycarbonate polyurethane CHRONOFLEX® AL 80A B-20, which comprises a reaction product of dicyclohexylmethane diisocyanate, a polycarbonate diol, and 1,4-butane diol.

12. A method of preparing the antimicrobial polyurethane composition of claim 1, the method comprising:
reacting in a reaction mixture a polyisocyanate and a polycarbonate polyol to produce a prepolymer;
reacting the prepolymer and a multihydroxyl alcohol or polyamine to produce a polyurethane composition; and
adding at least one silver ion associated with a carrier to the reaction mixture prior to complete polymerization.

13. The method of claim 12, wherein the carrier associated with the silver ion is zirconium phosphate.

14. The method of claim 12, wherein the carrier associated with the silver ion is a water soluble glass powder.

15. The method of claim 3, which further comprises the addition of at least one component selected from the group of micronized silica and barium sulfate.

16. The method of claim 14, which further comprises the addition of at least one component selected from the group of micronized silica and barium sulfate.

17. The method of claim 12, wherein the at least one silver ion associated with a carrier is added prior to prepolymer formation.

18. The method of claim 12, wherein the at least one silver ion associated with a carrier is added after prepolymer formation.

19. The method claim 12, which additionally comprises adding a catalyst.

20. A method for making a medical component for partial or complete insertion into a patient's body, the method comprising:
preparing an antimicrobial polyurethane composition according to the method of claim 12;
curing the antimicrobial polyurethane composition;
forming the antimicrobial polyurethane composition into pellets; and
forming the antimicrobial polyurethane pellets into a medical component.

21. A medical component for partial or complete insertion into a patient's body, the medical component comprising the antimicrobial polyurethane composition of claim 1.

22. An antimicrobial polyurethane composition comprising:
a reaction product of a polyisocyanate, a polyol, and a multihydroxyl alcohol or polyamine;
at least one silver ion associated with a zirconium phosphate carrier; and
barium sulfate;
wherein the barium sulfate and the silver ion associated with the zirconium phosphate carrier are added to the reaction product prior to complete polymerization; and
wherein the polymerized antimicrobial polyurethane composition exhibits substantially no leaching of silver ions as shown by the lack of formation of a zone of inhibition in a Kirby-Bauer test.

23. The antimicrobial polyurethane composition of claim 22, wherein the polyol is a polycarbonate glycol of the formula

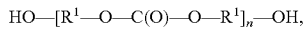

wherein $R^1$ is a linear chain of 2 to 20 carbon atoms, and n is 1000 to 2000.

24. The antimicrobial polyurethane composition of claim 22, wherein the polyol is hexanediolcarbonate glycol.

25. The antimicrobial polyurethane composition of claim 22, wherein the polyol is selected from the group consisting of polypropylene glycol, polytetramethylene glycol, and a dihydroxyl terminated polyester.

26. The antimicrobial polyurethane composition of claim 22, comprising a polyurethane polycarbonate CHRONOFLEX® AL 85A or CHRONOFLEX® AL 80A B-20, each of which comprises a reaction product of dicyclohexylmethane diisocyanate, a polycarbonate diol, and 1,4-butane diol.

27. The antimicrobial polyurethane composition of claim 26, which further comprises micronized silica.

28. A method of preparing the antimicrobial polyurethane composition of claim 22, the method comprising:
reacting in a reaction mixture a polyisocyanate and a polyol to produce a prepolymer;
reacting the prepolymer and a multihydroxyl alcohol or polyamine to produce a polyurethane composition; and
adding barium sulfate and at least one silver ion associated with a zirconium phosphate carrier to the reaction mixture prior to complete polymerization.

29. A method for making a medical component for partial or complete insertion into a patient's body, the method comprising:
preparing an antimicrobial polyurethane composition according to the method of claim 28;
curing the antimicrobial polyurethane composition;
forming the antimicrobial polyurethane composition into pellets; and
forming the antimicrobial polyurethane pellets into a medical component.

30. A medical component for partial or complete insertion into a patient's body, the medical component comprising the antimicrobial polyurethane composition of claim 22.

31. An antimicrobial polyurethane composition comprising:
a reaction product of a polyisocyanate, a polyol, and a multihydroxyl alcohol or polyamine;
silver ion-containing glass particles; and
barium sulfate;
wherein the barium sulfate and the silver ion-containing glass particles are added to the reaction product prior to complete polymerization; and
wherein the polymerized antimicrobial polyurethane composition exhibits substantially no leaching of silver ions as shown by the lack of formation of a zone of inhibition in a Kirby-Bauer test.

32. The antimicrobial polyurethane composition of claim 31, wherein the polyol is a polycarbonate glycol of the formula

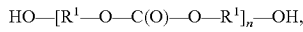

wherein $R^1$ is a linear chain of 2 to 20 carbon atoms, and n is 1000 to 2000.

33. A method of preparing the antimicrobial polyurethane composition of claim 31, the method comprising:
reacting in a reaction mixture a polyisocyanate and a polyol to produce a prepolymer;

reacting the prepolymer and a multihydroxyl alcohol or polyamine to produce a polyurethane composition; and
adding barium sulfate and silver ion-containing glass particles to the reaction mixture prior to complete polymerization.

34. A method for making a medical component for partial or complete insertion into a patient's body, the method comprising:
preparing an antimicrobial polyurethane composition according to the method of claim 33;
curing the antimicrobial polyurethane composition;
forming the antimicrobial polyurethane composition into pellets; and
forming the antimicrobial polyurethane pellets into a medical component.

35. A medical component for partial or complete insertion into a patient's body, the medical component comprising the antimicrobial polyurethane composition of claim 32.

* * * * *